United States Patent [19]

Stephens

[11] Patent Number: 5,604,933
[45] Date of Patent: Feb. 25, 1997

[54] HAND AND WRIST RESTRAINT FOR A PATIENT

[76] Inventor: Rusty Stephens, P.O. Box 622, Munford, Ala. 36268

[21] Appl. No.: 305,053

[22] Filed: Sep. 13, 1994

[51] Int. Cl.⁶ .................................................. A41D 13/10
[52] U.S. Cl. ........................................... 2/159; 2/162
[58] Field of Search ........................... 2/16, 159, 160, 2/162, 161.1, 161.2, 161.4, 161.6, 161.7, 910, 917; 128/879

[56] References Cited

U.S. PATENT DOCUMENTS

| | | | |
|---|---|---|---|
| 272,945 | 2/1883 | Chambers | 2/162 |
| 575,362 | 1/1897 | Luther | 2/162 |
| 1,385,715 | 7/1921 | Ross | 2/162 |
| 1,819,048 | 8/1931 | Till | 2/162 |
| 2,113,731 | 4/1938 | Kennedy | 2/162 |
| 2,280,467 | 4/1942 | Blanc | 2/162 |
| 2,314,545 | 3/1943 | Lindfelt | 2/159 |
| 2,508,031 | 5/1950 | Kennedy | 2/162 |
| 3,490,074 | 1/1970 | Hardy | 2/16 |
| 3,504,379 | 4/1970 | Glick | 2/16 |
| 3,741,207 | 6/1973 | Fuson | 2/910 |
| 3,970,081 | 7/1976 | Applegate, Jr. | 2/16 |
| 4,805,242 | 2/1989 | Bolton | 2/160 |
| 5,197,149 | 3/1993 | Overton | 2/162 |
| 5,328,449 | 7/1994 | Andrews et al. | 2/161.7 |

FOREIGN PATENT DOCUMENTS

| | | | |
|---|---|---|---|
| 1160518 | 7/1958 | France | 2/162 |
| 1162812 | 9/1958 | France | 2/162 |

OTHER PUBLICATIONS

"Self–Adhening Nylon Taples", *Journal of American Medical Assoc.*, vol. 168, No. 7, Oct. 18, 1958.

Primary Examiner—Amy B. Vanatta

[57] ABSTRACT

A hand and wrist restraint for a patient comprising: a glove having an inboard end and an outboard and a central extent positionable over the palm and back of the hand, the glove having a forward extent formed with elongated finger portions having openings at their outboard end for the passage of the fingers and thumb of the wearer therethrough, the glove having an opening at the inboard end positionable around the wrist of the user; and a strap secured to the glove adjacent to the inboard end adjacent to one side of the wrist, the strap having a remote free end and a securement end passing through an aperture in the glove and secured to an interior surface thereof.

1 Claim, 4 Drawing Sheets

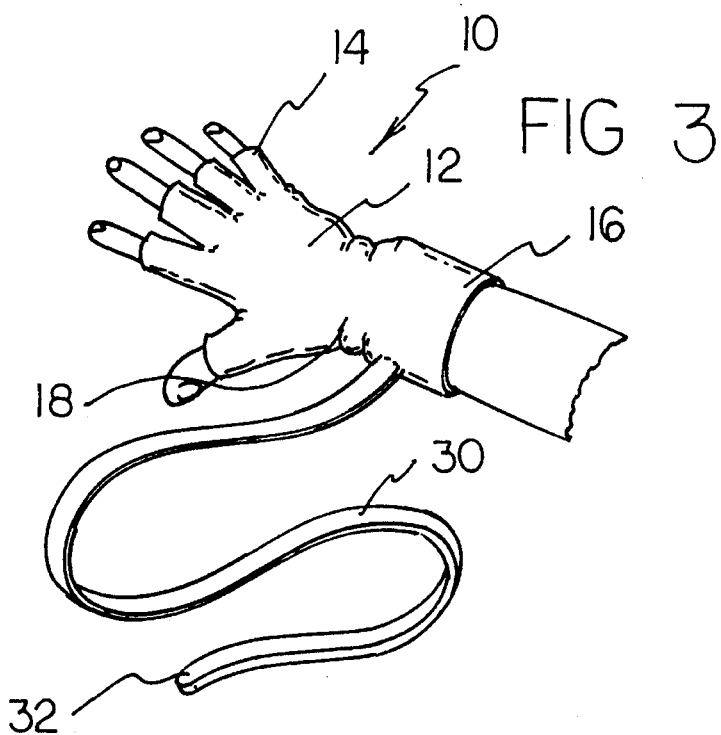
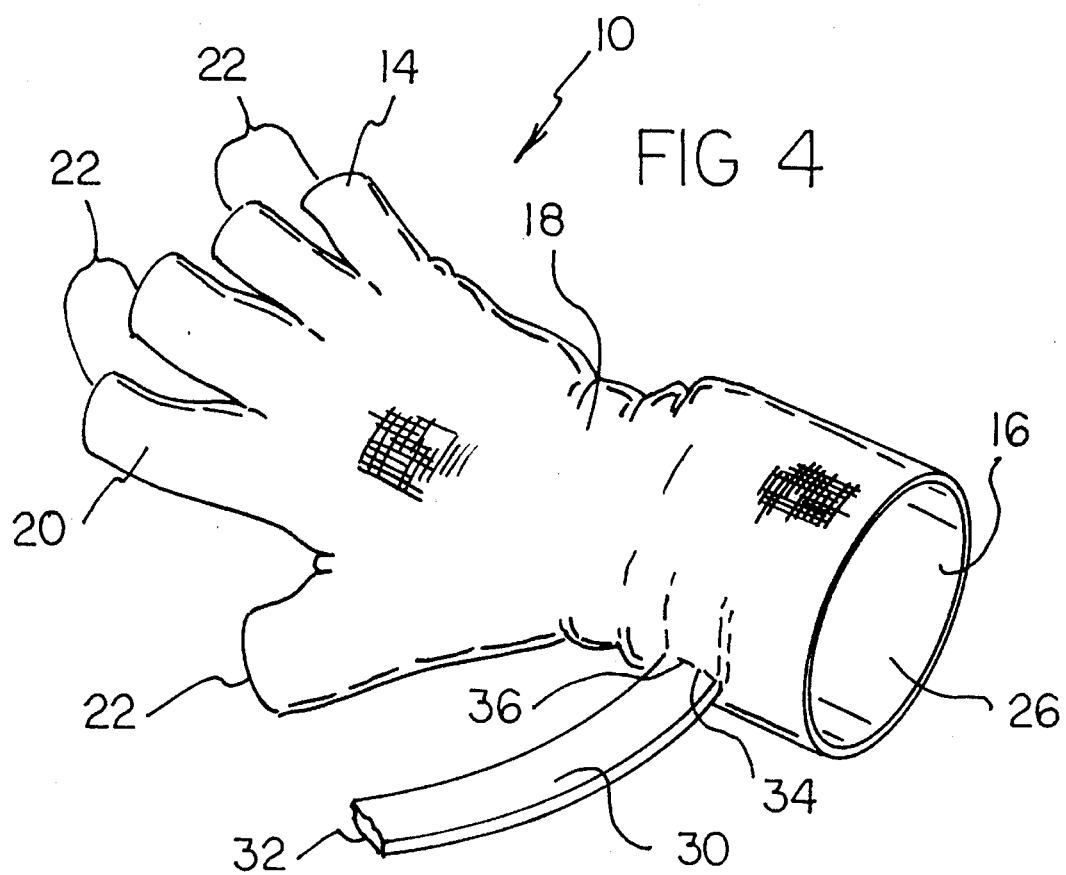

FIG 7
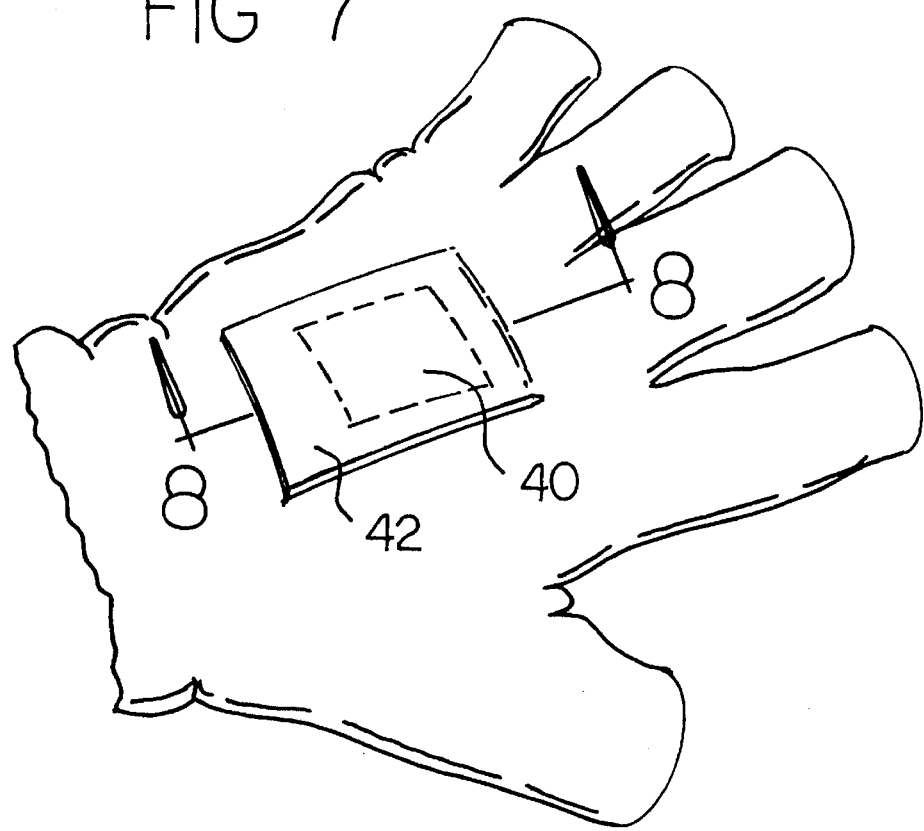
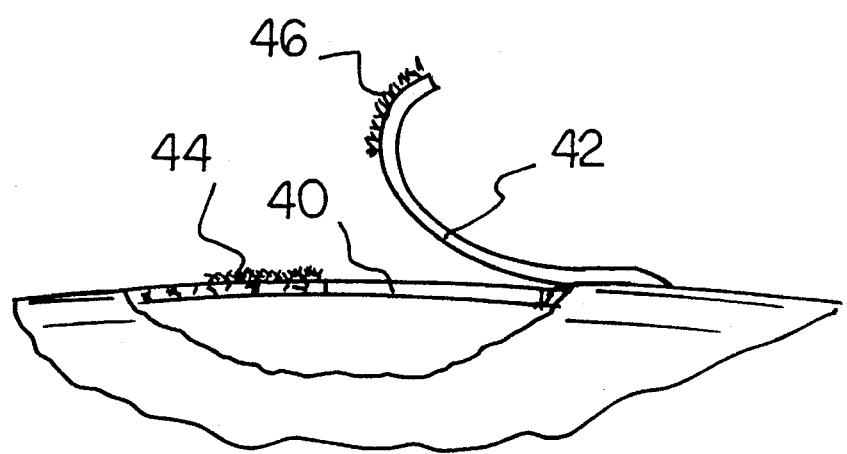
FIG 8

HAND AND WRIST RESTRAINT FOR A PATIENT

BACKGROUND OF THE INVENTION

1. Field of the Invention

The present invention relates to a hand and wrist restraint for a patient and more particularly pertains to restraining the movement of the patient's arms by restraint applied to the wrist through a glove having straps extending therefrom in the wrist area.

2. Description of the Prior Art

The use of restraints for combative patients of a wide variety of designs and configurations is known in the prior art. More specifically, restraints for combative patients of a wide variety of designs and configurations heretofore devised and utilized for the purpose of restraining the movement of patients in a combative mode through the use of a wide variety of methods and apparatuses are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 3,741,207 a band restraining mitt.

U.S. Pat. No. 4,024,863 discloses a hand restraining device.

U.S. Pat. No. 4,469,096 discloses a supplemental hand restraint device.

U.S. Pat. No. 4,887,616 discloses a restraint mitt for restraining a wearer's hand and arm.

U.S. Pat. No. 5,121,743 discloses a hand restraining device.

In this respect, the hand and wrist restraint for a patient according to the present invention substantially departs from the conventional concepts and designs of the prior art, and in doing so provides an apparatus primarily developed for the purpose of to restraining the movement of the patient's arms by restraint applied to the wrist through a glove having straps extending therefrom in the wrist area.

Therefore, it can be appreciated that there exists a continuing need for a new and improved hand and wrist restraint for a patient which can be used for to restrain the movement of the patient's arms by restraint applied to the wrist through a glove having straps extending therefrom in the wrist area. In this regard, the present invention substantially fulfills this need.

SUMMARY OF THE INVENTION

In view of the foregoing disadvantages inherent in the known types of restraints for combative patients of a wide variety of designs and configurations now present in the prior art, the present invention provides an improved hand and wrist restraint for a patient. As such, the general purpose of the present invention, which will be described subsequently in greater detail, is to provide a new and improved hand and wrist restraint for a patient and method which has all the advantages of the prior art and none of the disadvantages.

To attain this, the present invention essentially comprises a new and improved hand and wrist restraint for a patient comprising, in combination: a glove fabricated of cotton and having an inboard end and an outboard and a central extent positionable over the palm and back of the hand, the glove having a forward extent formed with elongated finger portions having openings at their outboard end for the passage of the fingers and thumb of the wearer therethrough, the glove having an opening at the inboard end positionable around the wrist of the user; a nylon strap secured to the glove adjacent to the inboard end adjacent to one side of the wrist, the strap having a remote free end and a securement end passing through an aperture in the glove and secured to an interior surface thereof; an opening formed in the central portion of the glove overlying the back of the hand of the wearer; and an associated rectangular flap pivotally secured to one side thereof and with pile-type fasteners on the glove and the flap in facing relationship adjacent to the edge thereof remote from the hinge to allow for the opening and closing of the opening.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hand and wrist restraint for a patient which have all the advantages of the prior art restraints for combative patients of a wide variety of designs and configurations and none of the disadvantages.

It is another object of the present invention to provide a new and improved hand and wrist restraint for a patient which may be easily and efficiently manufactured and marketed.

It is further object of the present invention to provide a new and improved hand and wrist restraint for a patient which are of durable and reliable constructions.

An even further object of the present invention is to provide a new and improved hand and wrist restraint for a patient which are susceptible of a low cost of manufacture with regard to both materials and labor, and which accordingly are then susceptible of low prices of sale to the consuming public, thereby making such hand and wrist restraint for a patient economically available to the buying public.

Still yet another object of the present invention is to provide a new and improved hand and wrist restraint for a patient which provides in the apparatuses and methods of the prior art some of the advantages thereof, while simultaneously overcoming some of the disadvantages normally associated therewith.

Still another object of the present invention is to restrain the movement of the patient's arms by restraint applied to the wrist through a glove having straps extending therefrom in the wrist area.

Lastly, it is an object of the present invention to provide a new and improved hand and wrist restraint for a patient comprising: a glove having an inboard end and an outboard and a central extent positionable over the palm and back of the hand, the glove having a forward extent formed with elongated finger portions having openings at their outboard end for the passage of the fingers and thumb of the wearer therethrough, the glove having an opening at the inboard end positionable around the wrist of the user; and a strap secured to the glove adjacent to the inboard end adjacent to one side of the wrist, the strap having a remote free end and a securement end passing through an aperture in the glove and secured to an interior surface thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a perspective illustration of the preferred embodiment of the hand and wrist restraint for a patient constructed in accordance with the principles of the present invention.

FIG. 4 is an enlarged perspective view of the device shown in FIG. 3.

FIG. 7 is a perspective view of a restraint constructed in accordance with an alternate embodiment of the invention.

FIG. 8 is a cross-sectional view taken along line 8—8 of FIG. 7.

The same reference numerals refer to the same parts through the various Figures.

DESCRIPTION OF THE PREFERRED EMBODIMENT

Figure 1:
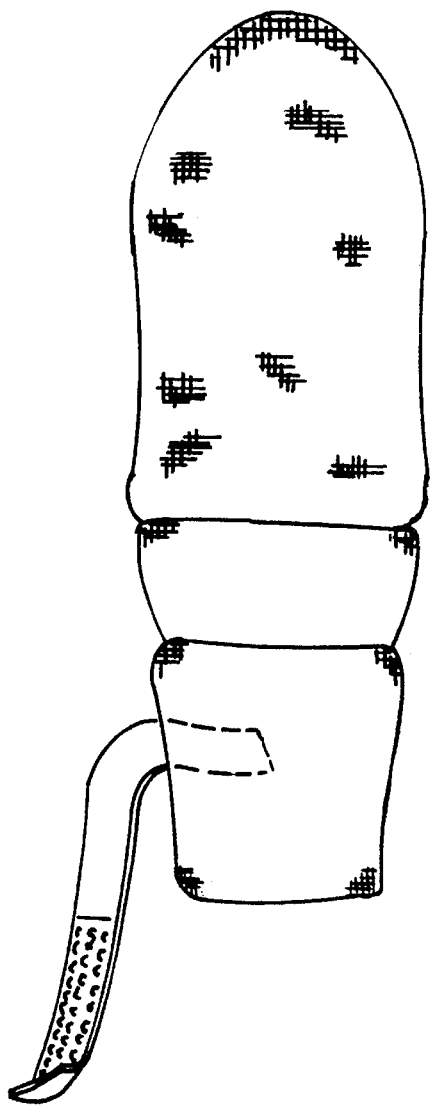
FIG. 1 is a perspective view of one type of restraint constructed in accordance with the prior art shown.
Figure 2:
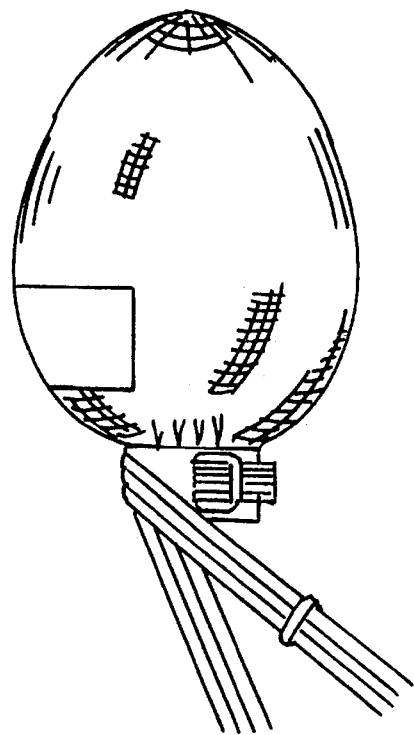
FIG. 2 is a side elevational view of a further type of restraint within the prior art.
Figure 5:
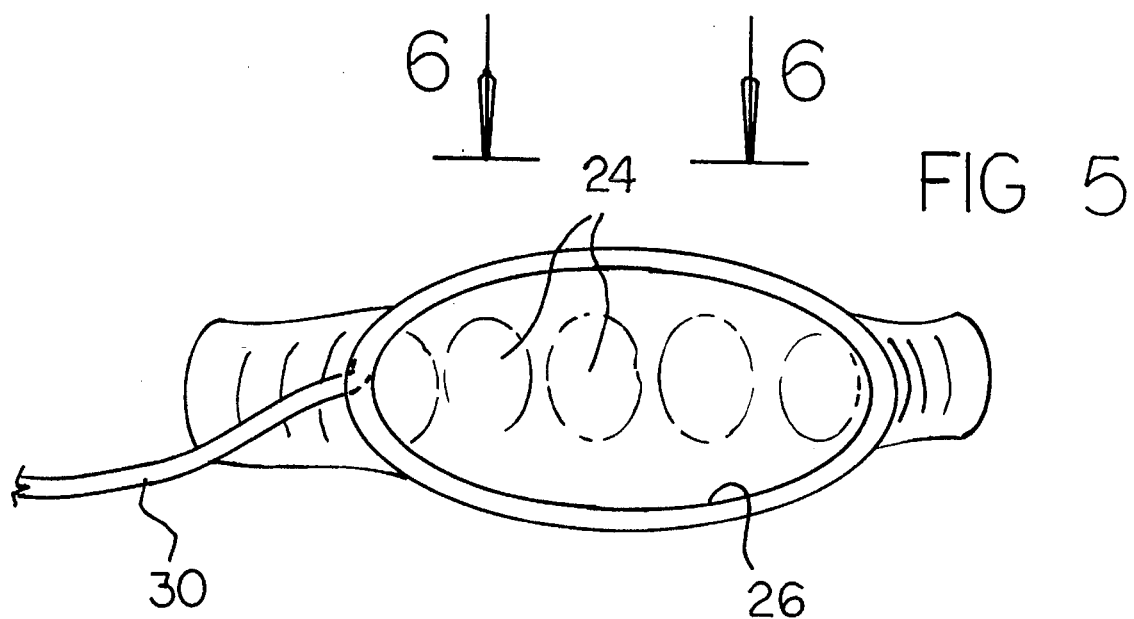
FIG. 5 is an end view of the device shown in FIGS. 3 and 4.
Figure 6:
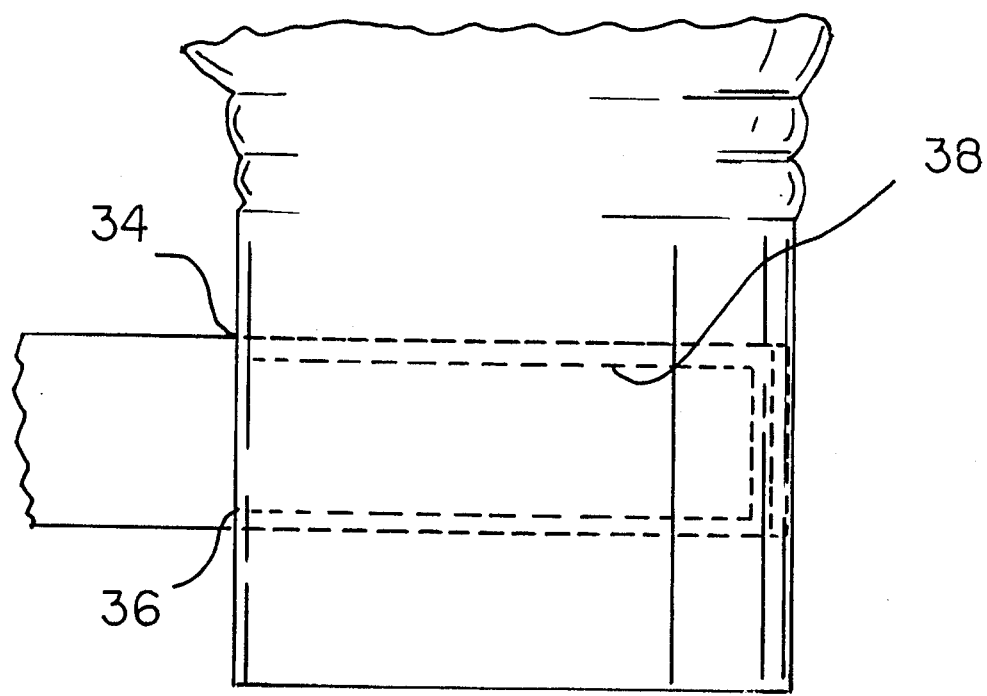
FIG. 6 is an enlarged viewing of the lower portion of the restraint taken along lines 6—6 of FIG. 5.

With reference now to the drawings, and in particular to FIG. 1 thereof, the preferred embodiment of the new and improved hand and wrist restraint for a patient embodying the principles and concepts of the present invention and generally designated by the reference numeral 10 will be described.

The present invention, the new and improved hand and wrist restraint for a patient comprised of a plurality of components. Such components include a glove, strap, opening and flap. Such components are individually configured and correlated with respect to each other so as to attain the desired objective.

The central component of the system 10 of the present invention is a glove 12. The glove is fabricated of a flexible material, preferably cotton. It has an outboard end 14 and an inboard end 16. A central extent 18 is located between the inboard and outboard ends and is positionable over the palm and back of the hand. The glove has a forward extent 20 formed with elongated finger portions 22. The finger portions have openings 24 at their outboard end for the passage of the leading ends of the fingers and thumb of a wearer. The glove also has an opening 26 at the inboard end positionable around the wrist of a wearer. Such opening is to allow the glove to be donned and removed from the wearer.

Next provided is a strap 30. The strap is preferably fabricated of an inextensible material such as nylon. It is secured to the glove adjacent to the outboard end and adjacent to one side of the wrist. The strap has a remote free end 32 and a securement end 34. The securement end is adapted to pass through an aperture 36 in the glove. Thereafter it is secured as by stitching 38 to an interior surface of the glove. In the embodiment shown in FIGS. 7 and 8, an opening 40 is formed in the central portion of the glove to overlie the back of the hand of the wearer. Such opening is adapted to allow a health care provider to have access to the back of the hand of the wearer for an inspection, injection, etc. purposes.

In association with the opening is a rectangular flap 42. Such flap is pivotally secured to one side of the opening. In addition, a pile-type fastener 44 on the glove and an associated pile-type fastener 46 is provided on the flap. The pile-type fasteners are in facing relationship with each other. They are located on the edges of the opening and flap remote from the hinge. The flap allows for the opening and closing of the opening in the glove.

The present invention is a cotton glove with a soft leather wrist restraint and nylon strap attached to it. The fingers are exposed for accessibility to the nails. This arrangement provides a very effective restraint to prevent combative patients from creating problems, such as tearing out intravenous lines and needles.

With the restraint around the wrist and the glove on the hand there is also little likelihood that the restraint can slide up and impair the circulation. Flaps with hook and loop closures may be added so they can be lifted up to check intravenous sites.

Patients are more comfortable when they are restrained by these soft gloves and wristbands. They do not irritate the skin and they can be worn for long periods of time without causing any difficulty.

Of course, the most important feature of these restraints is that they are very effective. The patient has a reasonable amount of freedom but is unable to remove or dislodge them. Rather than feeling tied and trapped, the patient senses a gentle persuasion for their own good and well being. The present invention is inexpensive and disposable, so it can be changed frequently and quickly without disturbing the patient.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved hand and wrist restraint for a patient wearer comprising, in combination:

a glove having a thickness, the glove fabricated of cotton and having an inboard end and an outboard end and a central extent positionable over the palm and back of the hand, the glove having a forward extent formed with elongated finger portions having openings at their outboard end for the passage of the fingers and thumb of the wearer therethrough, the glove having an opening at the inboard end positionable around the wrist of the wearer;

a nylon strap secured to the glove adjacent to the inboard end adjacent to one side of the wrist, the strap having a remote free end and a securement end passing through an aperture in the glove and secured to an interior surface thereof;

an opening formed through the entire thickness of the glove, the opening formed in the central portion of the glove with edges in a rectangular configuration and overlying the back of the hand of the wearer; and an associated rectangular flap with edges in a rectangular configuration and pivotally secured to an adjacent edge of the opening and forming a hinge and with pile-type fasteners on the glove and the flap in facing relationship adjacent to adjacent edges of the opening and flap remote from the hinge to allow for the opening and closing of the opening.

* * * * *